United States Patent
Gamperling et al.

(10) Patent No.: US 10,890,784 B2
(45) Date of Patent: Jan. 12, 2021

(54) METHODS, DEVICES, AND COMPUTER PROGRAM FOR DETERMINING A NEAR-VISION POINT

(71) Applicant: Carl Zeiss Vision International GmbH, Aalen (DE)

(72) Inventors: Michael Gamperling, Leipheim (DE); Cristina Alvarez Diez, Aalen (DE); Carsten Glasenapp, Oberkochen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 16/707,112

(22) Filed: Dec. 9, 2019

(65) Prior Publication Data

US 2020/0110280 A1    Apr. 9, 2020

Related U.S. Application Data

(63) Continuation of application No. PCT/EP2018/065177, filed on Jun. 8, 2018.

(30) Foreign Application Priority Data

Jun. 8, 2017  (EP) .................................... 17174925

(51) Int. Cl.
*G02C 7/02*   (2006.01)
*G02C 13/00*  (2006.01)
(Continued)

(52) U.S. Cl.
CPC ............ *G02C 7/027* (2013.01); *A61B 3/0025* (2013.01); *A61B 3/0091* (2013.01); *A61B 3/113* (2013.01); *A61B 3/14* (2013.01)

(58) Field of Classification Search
CPC ..... G02C 7/027; G02C 13/005; A61B 3/0025; A61B 3/0041; A61B 3/0058;
(Continued)

(56) References Cited

U.S. PATENT DOCUMENTS 6,944,320 B2    9/2005  Liu et al.
7,149,330 B2   12/2006  Liu et al.
(Continued)

FOREIGN PATENT DOCUMENTS

CN    103827735 A    5/2014
CN    105992966 A   10/2016
(Continued)

OTHER PUBLICATIONS

DIN EN ISO 7998:2006-01 "Ophthalmic optics—Spectacle frames—Lists of equivalent terms and vocabulary," DIN Deutsches Institut für Normung e.V., 2006.
(Continued)

*Primary Examiner* — Jordan M Schwartz
(74) *Attorney, Agent, or Firm* — Thrive IP®; Georg M. Hasselmann

(57) ABSTRACT

Methods, devices, and computer programs for determining a near-vision point of a person are disclosed. The person under examination looks at a movable near-vision target, and an image of the person is captured with a camera device incorporated into the near-vision target. The orientation and/or position of the near-vision target is determined. The near-vision point is then determined from the orientation and/or position of the near-vision target.

29 Claims, 6 Drawing Sheets

(51) Int. Cl.
*A61B 3/00* (2006.01)
*A61B 3/113* (2006.01)
*A61B 3/14* (2006.01)

(58) Field of Classification Search
CPC ......... A61B 3/0091; A61B 3/10; A61B 3/113; A61B 3/14; A61B 3/0075
See application file for complete search history.

(56) References Cited

U.S. PATENT DOCUMENTS

| | | | |
|---|---|---|---|
| 7,740,355 B2 | 6/2010 | Sessner et al. | |
| 9,759,934 B2 | 9/2017 | Divo et al. | |
| 9,971,172 B2 | 5/2018 | Cabeza-Guillen et al. | |
| 10,036,902 B2 | 7/2018 | Baranton et al. | |
| 10,564,446 B2 | 2/2020 | Nieuwenhuis et al. | |
| 2002/0105530 A1 | 8/2002 | Waupotitsch et al. | |
| 2003/0123026 A1 | 7/2003 | Abitbol et al. | |
| 2010/0149486 A1 | 6/2010 | Sayag | |
| 2010/0309428 A1* | 12/2010 | Altheimer | G02C 7/061 351/159.42 |
| 2014/0009737 A1 | 1/2014 | Kweon | |
| 2014/0293219 A1 | 10/2014 | Haddadi et al. | |
| 2015/0055085 A1 | 2/2015 | Fonte et al. | |
| 2016/0011437 A1 | 1/2016 | Nishimura et al. | |
| 2016/0327811 A1 | 11/2016 | Haddadi et al. | |
| 2016/0327813 A1* | 11/2016 | Baranton | G02C 7/027 |
| 2018/0307059 A1 | 10/2018 | Rousseau et al. | |
| 2019/0146243 A1* | 5/2019 | Parandian | G06Q 30/0633 351/159.75 |
| 2020/0018994 A1 | 1/2020 | Nieuwenhuis et al. | |
| 2020/0103675 A1 | 4/2020 | Schwarz et al. | |

FOREIGN PATENT DOCUMENTS

| | | |
|---|---|---|
| DE | 10300188 A1 | 7/2004 |
| DE | 102005003699 A1 | 7/2006 |
| DE | 102011009646 A1 | 8/2012 |
| DE | 102014200637 A1 | 7/2015 |
| EP | 1038495 A2 | 9/2000 |
| EP | 2913704 A1 | 9/2015 |
| EP | 2963482 A1 | 1/2016 |
| EP | 3270099 A1 | 1/2018 |
| EP | 3355100 A1 | 8/2018 |
| EP | 3355102 A1 | 8/2018 |
| EP | 3355104 A1 | 8/2018 |
| EP | 3355214 A1 | 8/2018 |
| EP | 3410178 A1 | 12/2018 |
| FR | 3021205 A1 | 11/2015 |
| JP | 2003329541 A | 11/2003 |
| JP | 2005342186 A | 12/2005 |
| WO | 2014061294 A1 | 4/2014 |
| WO | 2017064060 A1 | 4/2017 |

OTHER PUBLICATIONS

DIN EN ISO 8624:2015-12 "Ophthalmic optics—Spectacle frames—Measuring system and terminology," DIN Deutsches Institut für Normung e.V., Dec. 2015.
DIN EN ISO 13666:2012 "Ophthalmic optics—Spectacle lenses—Vocabulary (ISO 13666:2012)," German and English version EN ISO 13666:2012, Oct. 2013.
"Bildwinkel [Angle of view]," Wikipedia online encyclopedia entry [retrieved on Apr. 19, 2020], and English-language counterpart entry thereof, retrieved from the Internet using <URL: de.wikipedia.org/wiki/Bildwinkel>, last edited Apr. 1, 2020.
Dedek "Entwurf and Implementierung einer Objektverfolgung unter Verwendung einer Smart-Camera mit PTZ-Funktionalitat [Design and implementation of object tracking using a smart camera with PTZ functionality]", bachelor dissertation 2009, available at the url: www.ipi.uni-hannover.de/fileadmin/institut/pdf/Abschlussarbeiten/Bachelorarbeit_Dedek_2009.pdf, relevance found in paragraph [0068] of the specification, 2009.
Hirschmüller et al.: "Stereo Processing by Semiglobal Matching and Mutual Information," in IEEE Transactions on Pattern Analysis and Machine Intelligence, vol. 30, No. 2, pp. 328-341, doi: 10.1109/TPAMI.2007.1166, Feb. 2008.
"Metadaten [Metadata]," Wikipedia online encyclopedia entry [retrieved on Jan. 31, 2020], and English-language counterpart entry thereof, retrieved from the Internet using <URL: de.wikipedia.org/wiki/Metadaten>, last edited Jan. 1, 2020.
Mora et al.: "Gaze estimation from multimodal Kinect data", IEEE Computer Society Conference on Computer vision and pattern recognition workshops (CVPRW), pp. 25-30, 2012, IEEE, XP032206804, Jun. 16, 2012.
Niessner et al. "Real-time 3D reconstruction at scale using voxel hashing," ACM Trans. Graph. 32, 6, Article 169, available at the url doi.org/10.1145/2508363.2508374, Nov. 2013.
Rau et al. "A Semi-Automatic Image-Based Close Range 3D Modeling Pipeline Using a Multi-Camera Configuration," Sensors (Basel, Switzerland), 2012;12(8), in particular p. 11289, figure "Fig.16," doi:10.3390/s120811271, Aug. 14, 2012.
International Search Report and English-language translation thereof issued in PCT/EP2018/065177, which is a counterpart hereof, dated Oct. 2, 2018.
International Preliminary Examination Report and English-language translation thereof issued in PCT/EP2018/065177, which is a counterpart hereof, completed Jan. 10, 2020.
ISO 8373:2012(E/F) "Robots and robotic devices—Vocabulary," ISO, 2012.
Bennett et al.: "Clinical Visual Optics," Third Edition, pp. 142 to 145, Oxford (1998).
Office Action by the Chinese Patent Office issued in CN20188005153513, dated Aug. 14, 2020, and English-language translation thereof.

* cited by examiner

METHODS, DEVICES, AND COMPUTER PROGRAM FOR DETERMINING A NEAR-VISION POINT

CROSS REFERENCE TO RELATED APPLICATIONS

This application is a continuation application of international application PCT/EP2018/065177, filed Jun. 8, 2018, which claims priority to European patent application EP 17174925.2, filed Jun. 8, 2017, both of which are hereby incorporated by reference in their entireties.

TECHNICAL FIELD

The present application relates to methods, devices, and corresponding computer programs for determining near-vision points of spectacle lenses.

BACKGROUND

Fitting spectacle lenses in spectacle frames requires centration parameters to fit the position of the spectacle lens in the spectacle frame in a manner adapted to the respective person for whom the spectacles are intended. Centration parameters of this type are defined inter alia in DIN EN ISO 13666:2012. The centration parameters include distance-vision points, which specify where a viewing direction of the person when looking into the distance passes through the spectacle lenses, and near-vision points, which specify where a viewing direction of the person for near vision, e.g., when reading, passes through the spectacle lenses. Distance-vision point and near-vision point are defined in particular in DIN EN ISO 13666: 2012 under 5.16 and 5.17. The near-vision point is required in progressive lenses, which enable a correction for distance vision and a correction for near vision depending on the viewing direction (cf. DIN EN ISO 13666: 2012, 8.3.5). Nowadays, progressive lenses of this type are often bought and incorporated into a spectacle frame without the position of the near-vision points being determined, which can have the effect that the wearer of spectacles sees objects nearby poorly.

In order to rectify this problem, various approaches are known for determining near-vision points.

JP 2005-342186 A discloses for example a method which uses movable light sources that move from a distance viewing direction (horizontally from the head of the person to be examined) to a near viewing direction inclined with respect to the horizontal. A plurality of image recordings are created in the process. Here the viewing directions are predefined by the movable light sources.

US 2014/0009737 A1 discloses a relatively complex device for determining near and distance centration data. Two camera modules are used here to record images of a person to be examined for a distance viewing direction and a near viewing direction. For this purpose, software can be installed on a tablet computer and elements to be viewed by the person to be examined can be displayed on a screen of the tablet computer. A scale additionally has to be attached to the head of the person to be examined.

US 2010/0149486 A1 measures a difference in forward inclination of the head between a distance viewing direction and a reading viewing direction, wherein the exact viewing direction for reading is not determined, which can result in inaccuracies.

US 2003/0123026 A1 determines a near pupillary distance (PD) on the basis of a front recording of the head of the person to be examined. The device used in that case has a short viewing distance, which can result in the pupils being concealed by parts of the spectacle frame.

DE 103 00 188 A1 discloses a method in which near centration parameters are determined by means of image recordings, the document not specifying exactly how the determination is intended to be carried out.

Most of the procedures described above have the disadvantage that a reference object having known dimensions, for example a so-called measuring brace, has to be arranged on the spectacle frame or on the face in order to identify the arrangement of the spectacle frame in space. However, the use of such a measuring brace constitutes not inconsiderable influencing of the position of the frame in the person's face, and the person himself/herself may be influenced by the presence of the measuring brace, with the result that inaccuracies during the measurement may arise here. Moreover, the near-vision points are determined only indirectly in some instances in these methods.

EP 2 913 704 A1 discloses a device which makes it possible to determine centration parameters for a distance viewing direction and a near viewing direction. In that case, the distance viewing direction and the near viewing direction are predefined by the device owing to dictates of design. Consequently, the near viewing direction predefined by the device does not necessarily correspond to the actual near viewing direction adopted by the person to be examined for example when reading.

WO 2014/061294 A1 discloses a method in which a head of a person to be examined is illuminated with stroboscopic light and is recorded in each case for a distance-vision position and a near-vision position by means of a camera, which is movable between distance-vision position and near-vision position. The reflections from the pupils that are generated by the stroboscopic light are then evaluated. In that case, too, the near-vision position does not necessarily correspond to the person's natural reading position, but rather is determined by the camera position. Moreover, stroboscopic illumination is required.

FR 3 021 205 A1 discloses a procedure for determining posture parameters in which a person is recorded during various activities, for example reading, and relative positions of the head in the postures are determined on the basis of corresponding points. A determination of centration parameters such as a near-vision point, for example, is not mentioned in the document.

DE 10 2011 009 646 A1 discloses a method for determining a near-vision point in which an image of a head of a person is recorded while the person is looking at a movable near-vision target. The position and/or the orientation of the near-vision target are/is determined and the near-vision point (51) is determined on the basis of the image and on the basis of the position and/or orientation of the near-vision target.

US 2002/0105530 A1 discloses generating a 3D model of a face by means of a camera system and a 3D modelling application, wherein a fully textured 3D model of the face is generated.

EP 2 963 482 A1 discloses a system for lens design. US 2014/0293219 A1 discloses a method for determining a person's reading distance.

The European application EP 3 270 099 A1 discloses a method for determining a corneal vertex distance on the basis of two lateral images of a head of a person, wherein a camera records a first lateral image with spectacles having been put on and a second lateral image without spectacles having been put on. European patent application No. 1 038

495 A2 discloses a method for determining a near-vision point and a device for determining a near-vision point.

SUMMARY

It is an object of the present application to make it possible to determine the viewing direction of a person without the use of measuring rods that need to be fitted to the spectacle frame or to the person.

For this purpose, according to a first aspect of the disclosure, a method for determining a near-vision point and a device for determining a near-vision point are provided.

DE 10 2014 200 637 A1 discloses a method for determining a near-vision point and a device method for determining a near-vision point. Proceeding from DE 10 2014 200 637 A1, it is an object of the present application to make it possible to determine the near-vision point without the use of lateral target marks and to make the method more robust vis à vis concealment of the eyes by a spectacle earpiece in the lateral image.

For this purpose, according to a second aspect of the disclosure, a method for determining a near-vision point and a device method for determining a near-vision point are provided.

Japanese patent publication No. 2003329541 A discloses a method for determining a near-vision point using a camera device and a near-vision target and a device for determining a near-vision point. Proceeding from Japanese patent publication No. 2003329541 A, it is another object of the present application to make it possible to determine the near-vision point without the use of lateral target marks and to enable a greater freedom of movement of the near-vision target.

For this purpose, according to that aspect of the disclosure, a method for determining a near-vision point using a camera device and a near-vision target and a device for determining a near-vision point are provided.

Exemplary embodiments of the disclosure are discussed below.

The aspects of the disclosure are discussed briefly below. Terms used are in some instances not defined until after this brief discussion.

In the first aspect of the disclosure, a method for determining a near-vision point is provided. The method comprises:
  recording an image of a head of a person, wherein recording the image is carried out by an image recording unit incorporated in the near-vision target while the person is looking at a near-vision target,
  wherein the image shows a pupil position and/or cornea position of eyes,
  wherein the near-vision target is movable, and wherein the method further comprises:
  determining an orientation of the near-vision target, and
  determining a viewing direction of the person when looking at the near-vision target on the basis of the image.

The method is characterized in that determining the near-vision point is carried out on the basis of the image and on the basis of the viewing direction, and on the basis of the position and/or orientation of the near-vision target wherein
  determining the viewing direction is based on a location of the pupil position and/or cornea position of the eyes relative to an axis of symmetry of the image recording unit and an image angle and a resolution of the image recording unit, wherein the direction of the axis of symmetry is determined by the orientation of the near-vision target.

Furthermore, in the first aspect of the disclosure, a device for determining a near-vision point is provided. The device comprises:
  a near-vision target (40; 60), which is movable and comprises an image recording unit (62) and a position detection unit (61),
  wherein the image recording unit (13; 62) is configured for recording an image of a person while the person is looking at a near-vision target,
  wherein the position detection unit (42; 61) is configured for determining an orientation of the near-vision target, and
  a computing unit (14) for determining the near-vision point.

The device is characterized in that the computing unit is configured in such a way that determining the near-vision point is carried out on the basis of the image and on the basis of the viewing direction, and on the basis of the position and/or orientation of the near-vision target wherein
  determining the viewing direction is based on a location of the pupil position of the eyes relative to an axis of symmetry of the image recording unit at an image angle and a resolution of the image recording unit, wherein the direction of the axis of symmetry is determined by the orientation of the near-vision target.

Such a method and such a device have the advantage over the method in European patent application No. 1 038 495 A2 that a viewing direction of the person can be determined without the need to use measuring rods that have to be fitted to the spectacle frame or to the person, since here the viewing direction is effected on the basis of the recorded image and properties of the image recording unit, namely resolution and image angle.

A determination on the basis of or based on one or a plurality of variables (e.g., image angle and resolution) means that these variables influence the determination. Concrete examples of the determination will be explained later.

In this case, an image recording unit is generally a unit that can create a digital image of an object, in this case a head of a person or a part thereof. An image recording unit of this type can comprise one or a plurality of cameras.

The resolution of the image recording unit specifies how many pixels a digital image thus generated has. In the case of customary rectangular images, the resolution is usually specified in L×H, wherein L and H specify the number of pixels along the edges of the image. Such a rectangular image can be regarded as a pixel matrix having length L and width H. In this case, the resolution is dependent on an image sensor used.

Axis of symmetry of the camera is understood to mean an axis of the camera at which a light ray incident along the axis of symmetry is imaged in the center of the image. Upon a rotation of the camera about the axis of symmetry, the observed direction of recorded objects, measured as an angle relative to the axis of symmetry, does not change. In many image recording units, the axis of symmetry corresponds to the optical axis of a lens of the image recording unit.

The image angle specifies the angular range in which as viewed by the image recording unit objects are captured in the image and corresponds to the customary use of this term in photography; see, for example, at the url de.wikipedia.org/wiki/Bildwinkel; version as of May 6, 2018. The image angle is likewise determined by a lens used.

As a result of resolution and image angle, there is a fixed relationship between an angle at which an object is situated with respect to the axis of symmetry of the image recording unit as viewed by the image recording unit and the pixel or pixels at which the object appears in the image. Thus, by identifying e.g., a location of an eye or part thereof in the image, it is possible to determine the viewing direction relative to the axis of symmetry.

In the second aspect of the disclosure, a method for determining a near-vision point is provided. The method comprises:
  recording a front image and a first lateral image of a head of a person while the person is wearing a spectacle frame and looking at a near-vision target, wherein the near-vision target is movable,
  determining a position and orientation of the near-vision target,
  determining a location of the spectacle frame on the basis of the front image and the lateral image, and
  determining a viewing direction of the person when looking at the near-vision target, and determining the near-vision point of the spectacle frame on the basis of the viewing direction and the location of the spectacle frame.

The method is characterized in that determining the viewing direction comprises: generating a second lateral image of the head on the basis of a 3D model of the head,
  determining the position of a pupil and/or a cornea of an eye of the person on the basis of the first lateral image and the second lateral image,
  calculating the viewing direction as a difference between the position of the near-vision target and the position of the pupil or the cornea and the first image.

In contrast to EP 3 270 099 A1 cited in the introduction, the second lateral image here is thus generated from a 3D model and not recorded by means of a camera.

Furthermore, in the second aspect of the disclosure, a device for determining a near-vision point (51) is provided. The device comprises:
  a near-vision target (40; 60), wherein the near-vision target (40; 60) is movable,
  an image recording unit (13; 62) for recording a front image and a first lateral image of a head of a person while the person is looking at the near-vision target,
  a position detection unit (42; 61) for determining a position and orientation of the near-vision target, and
  a computing unit (14) for determining the near-vision point.

The device is characterized in that the computing unit (14) is configured for:
  generating a first lateral image of the head on the basis of a 3D model of the head,
  determining the position of a pupil and/or a cornea of an eye of the person on the basis of the first lateral image and the second lateral image, and
  calculating the viewing direction as a difference between the position of the near-vision target and the position of the pupil or the cornea and the first image.

Such a method and such a device have the advantage over the method in DE 10 2014 200 637 A1 that the determination of the near-vision point is made possible without the use of lateral target marks and that the method can be applied successfully even in such cases when the eyes of the person on the lateral image are concealed by a spectacle earpiece.

Difference is understood to mean a subtraction of vectoral quantities.

Typically, the method according to the second aspect of the disclosure is characterized in that determining the position of the pupil and/or the cornea on the basis of the first lateral image and the second lateral image comprises bringing the first lateral image to congruence with the second lateral image. The bringing to congruence enables image regions of the first lateral image and of the second lateral image to be identified easily with one another with regard to their location.

Typically, the method is additionally or alternatively characterized in that determining the position of the pupil and/or the cornea on the basis of the first lateral image and the second lateral image comprises replacing a part of the first lateral image by a corresponding part of the second lateral image that includes the pupil and/or cornea. In this regard, it is possible to identify the location of pupil and/or cornea in the first lateral image even if pupil and/or cornea in the first lateral image are/is concealed initially by a spectacle earpiece.

Replacing a part of the first lateral image is understood here to mean that items of information of the first lateral image are replaced by items of information of the second lateral image in a location-selective manner. By way of example, it is possible to represent lateral images as pixel matrices in two dimensions with two indices x and y. In this case, replacing a part can mean that individual pixel values for specific x- and y-values xi and yi of the first lateral image are replaced by raster matrix values of the second lateral image for the same x- and y-values xi and yi.

The first and second lateral images can be represented in particular on displays, for example a screen, for viewing by an optician.

The device according to the second aspect of the disclosure can typically be configured in accordance with the above preferred embodiments of the method.

Such a procedure in which the position of pupil and/or cornea is determined by the first lateral image and the second lateral image can also be applied in the first aspect of the disclosure. In this case, the determination of the viewing direction can additionally be carried out on the position of pupil and/or cornea thus determined. In particular, a position of the eye center of rotation can be deduced from the position of pupil and/or cornea, as will be explained in greater detail later, and the viewing direction can then be determined such that it "starts" at the eye center of rotation, that is to say runs proceeding from the eye center of rotation.

In the third aspect of the disclosure, a method for determining a near-vision point is provided. The method comprises:
  recording an image of a head of a person while the person is looking at a near-vision target, wherein the near-vision target is movable.

The method is characterized in that the near-vision target has a movable mechanical connection to a column comprising at least one sensor, and in that the method further comprises:
  determining a position and/or orientation of the near-vision target (40) in space by means of the at least one sensor, and
  determining the near-vision point on the basis of the image and on the basis of the position and/or orientation of the near-vision target.

Furthermore, in the third aspect of the disclosure, a device for determining a near-vision point is provided. The device comprises:
  a near-vision target, wherein the near-vision target is movable, an image recording unit (13; 62) for recording an image of a head of a person while the person is looking at the near-vision target, and
  a computing unit (14) for determining the near-vision point.

The device is characterized in that the near-vision target (40) has a movable mechanical connection (42) to a column (12) comprising at least one sensor configured to determine a position and orientation of the near-vision target and to provide them to the computing unit (14).

Such a method and such a device have the advantage over the method in Japanese patent publication No. 2003329541 A that the determination of the near-vision point without the use of lateral target marks is made possible and that the person can move the near-vision target over a large range in order to attain a pleasant reading posture.

In the case of the above methods and devices of the first and third aspects, the images discussed can be recorded while the person is wearing a spectacle frame, or can be recorded when the person is not wearing a spectacle frame. As will be explained in greater detail later, in the first case it is then possible to determine a location of the spectacle frame from the images, while in the latter case the location of the spectacle frame is determinable virtually on the basis of a model.

It should be noted that the reference to "a near-vision point" here means that the near-vision point can be determined for one eye or for both eyes of the person.

The position of the near-vision target should be understood to mean the position in three-dimensional space such as can be specified for example in Cartesian coordinates in relation to a spatially fixed coordinate system. The orientation of the near-vision target describes how the near-vision target is oriented at its position, for example the direction in which a side of the near-vision target faces at which the person is intended to look for measurement purposes. The combination of position and orientation is also referred to as pose in accordance with DIN EN ISO 8373: 2012-03 and is of great importance in particular in robotics as well.

A near-vision target is an article at which the person is intended to look for the purpose of determining the near-vision point, wherein for example a reading posture can be adopted. For this purpose, the near-vision target can have a text to be read or an image to be viewed, which the person is intended to view with a normal reading posture. By virtue of the fact that the near-vision target is movable, a natural reading posture can be adopted, and the measurement is not restricted to a reading posture predefined by the device. The determination on the basis of the image and the position and/or orientation of the near-vision target additionally makes it possible to dispense with the use of a measuring brace or similar article.

Typically, determining the near-vision point comprises determining a viewing direction of the person when looking at the near-vision target on the basis of the image, wherein determining the near-vision point is carried out on the basis of the viewing direction. By means of the viewing direction, the near-vision point can be ascertained in a simple manner.

For this purpose, the method typically furthermore comprises determining a relative location of a spectacle frame worn by the person with respect to a eye center of rotation of the person.

In this regard, the near-vision point can easily be determined by ascertaining, proceeding from the eye center of rotation, a point of intersection of the viewing direction with a spectacle lens, the location of which is defined by the location of the spectacle frame. Moreover, in this way only the viewing direction is required, but not the distance between the person and the near-vision target, which distance can be chosen arbitrarily. Here, pursuant to DIN EN ISO 7998 and DIN EN ISO 8624, a spectacle frame should be understood to mean a frame or a holder by means of which spectacle lenses can be worn on the head. In particular, the term as used herein also includes rimless spectacle frames.

Determining the relative location of the spectacle frame worn by the person with respect to the eye center of rotation of the person can be carried out by means of further image recordings or the image recordings, for example in the course of image recordings created for determining the distance-vision point for which the person wears the spectacle frame. Corresponding devices which determine centration parameters such as the distance-vision point on the basis of a plurality of image recordings are described in European patent applications No. 17 153 559.4 and No. 17 153 556.0.

In this regard, with the aid of parameters such as the relative location of the spectacle frame worn by the person with respect to the eye center of rotation of the person, which are present anyway from a previous determination of the distance-vision point, a near-vision point can easily be determined.

From distance and near-vision points, it is then additionally possible to determine the so-called progression channel length (see 14.1.25 in DIN EN ISO 13666:2013-10), which specifies the distance between near-vision point and distance-vision point. Additionally or alternatively, it is possible to determine the nasal distance of the near-vision points relative to the distance-vision points. The nasal distance is sometimes referred to as "inset", but does not necessarily correspond to the inset that has been standardized in the meantime in DIN EN ISO 13666:2013-10 under 14.2.13. Conventionally, the nasal distance is fixedly predefined by the lens design of the progressive spectacle lens or of the bifocal spectacle lens. This does not take account of the fact that the nasal distance of both sides may possibly be asymmetrical, e.g., if the subject normally keeps the head slightly inclined laterally, but pivots the gaze for reading perpendicularly downward, without changing the lateral inclination of the head. Such an asymmetry can be ascertained by the determination of the nasal distance on the basis of the near-vision points and distance-vision points determined as described above.

In one variant, in this case the image is recorded as a recording of a plurality of images by the same camera unit by means of which the further image recordings are created. For this purpose, the camera unit described in European patent applications No. 17 153 559.4 and No. 17 153 556.0 cited above has a plurality of cameras arranged at an angle of approximately 90° with respect to one another in order to create front and lateral recordings. In a plurality of images recorded in this way, a location of the spectacle frame and an eye position can then be determined by means of the algorithms described in the applications above. This determination can be performed on the basis of a determination of the location of the spectacle frame in the further image recordings, i.e. the shape of the spectacle frame as determined there can be determined in the recorded image by means of image analysis algorithms as described in European patent application No. 17153651.9, for example, or a joint determination can be carried out. In particular, locations of lens edges of spectacle lenses which correspond to frame rims of the spectacle frame are detected in the case of the algorithms described in European patent application No. 17153651.9. As a result, the location of the spectacle frame, in particular the location of the frame plane (DIN EN ISO 13666:2012; 17.2), is likewise known. A determination of mutually corresponding elements, in this case of the spectacle frames, in the plurality of images and also in the further image recordings can also be carried out as described in U.S. Pat. No. 6,944,320 B2 or U.S. Pat. No. 7,149,330 B2. A robust determination of the location of the spectacle frame is possible in this way.

With the location of the spectacle frame, in particular the frame plane, the near-vision point can then be determined as described above.

Alternatively, the determination of the location of the spectacle frame can also be carried out jointly in the recorded image and the further image recordings. Joint processing of the image and of the further image recording in order to determine the spectacle frames, in particular the frame rims and thus the spectacle lenses, further increases the robustness of the method.

In the case of such a procedure using a camera unit, the position of the near-vision target in space can be detected for example by object tracking by means of further cameras or by a mechanical connection to the camera device, the mechanical connection being provided with sensors. Such object tracking is described e.g., in T. Dedek, "Entwurf and Implementierung einer Objektverfolgung unter Verwendung einer Smart-Camera mit PTZ-Funktionalitat [Design and implementation of object tracking using a smart camera with PTZ functionality]", bachelor dissertation 2009, available at the url www.ipi.uni-hannover.de/fileadmin/institut/pdf/Abschlussarbeiten/Bachelorarbeit_Dedek_2009.pdf.

The viewing direction can be determined in this case by determining pupil positions in three dimensions on the basis of the image and then determining the viewing direction as a difference between the position of the near-vision target and the position of the pupils. In this case, the position of the pupils can be determined by the methods determined in the applications cited above.

The abovementioned eye center of rotation (COR) can be determined with the aid of known empirical data (see, for example, Bennett, A., Rabbetts, R.: Clinical Visual Optics, Third Edition, Oxford (1998), pages 143/144) or taking account of a refraction-dependent location behind the pupil and it is thus possible to specify its position relative to the location of the spectacle frame and thus the frame rims. In this way, the determination is possible by means of conventional methods.

In another embodiment, recording the image is carried out by means of a camera incorporated in the near-vision target, and the orientation of the near-vision target and thus of the camera is determined by inclination sensors in the near-vision target. The pupil position of the eyes is then determined in the recorded image. With known image angle and resolution of the camera, which result from the specifications of the camera, it is possible, as indicated above for the first aspect, to specify for the pupils a direction relative to an axis of symmetry of the camera (which usually corresponds to the optical axis of the camera). The direction of the axis of symmetry results from the ascertained inclination of the near-vision target. Consequently, in this embodiment, it is possible directly to determine the viewing direction of both eyes, and, as explained above, on the basis of the viewing direction toward the near-vision target, a near-vision point for each eye.

The direction of the pupils can be specified here if the person looks directly into the camera. In other exemplary embodiments, the near-vision target can comprise a display region. In this case, display region is understood to mean a region on which items of information can be displayed, for example a screen. In this case, items of information can be images, drawings, text or optotypes, for example Landolt rings. In the case of a tablet computer or smartphone, the display region is for example the so-called display of the tablet or smartphone.

The display region can be arranged at a distance from the camera. In cases where the person looks at the display region, determining the viewing direction can additionally be based on a distance between the camera of the near-vision target and the display region or a part of the display region on which items of information are displayed. As a result, the accuracy of the method can be increased further; it is thus possible to take account of the fact that looking at the display region, which is at a distance from the camera, results in the actual viewing direction differing from the viewing direction which, as described above, is determined only on the basis of image angle and resolution of the camera.

Here in the case of such a correction which takes account of the fact that the person is looking at the display region rather than directly at the camera, the distance between the near-vision target and the person can be taken into account when determining the viewing direction. These corrections are then based on simple geometric considerations. In other exemplary embodiments, the person can look at the camera, i.e. the camera itself serves as a near-vision target.

The camera of the near-vision target can be intrinsically calibrated in order to correct image field distortions. Intrinsic calibration means that the image field distortion is measured and then corrected. This increases the accuracy of the determination of the near-vision point. If the accuracy of the determination is sufficient even without such a calibration, for example because the distortions are less than 10%, the intrinsic calibration of the camera of the near-vision target can also be omitted.

Typically, in such a case, a tablet computer or smartphone is used as the near-vision target. Such devices, with the front camera, possess a suitable camera and have built-in inclination sensors and a display for displaying a text to be read or an image to be viewed, for example, with the result that the method according to the disclosure can be implemented here by means of simple programming. The recorded image and the measured inclinations can then be evaluated directly in the tablet or smartphone or, by means of an interface such as is likewise usually present, can be sent in a wired or wireless manner to a computing unit for further evaluation.

The method can additionally comprise a correction of the determined viewing directions and/or of the ascertained near-vision point, such that an operator such as an optician can carry out a correction of these variables, i.e. of the viewing directions and/or of the near-vision point, for example if he/she is of the opinion that the person to be examined has not adopted the correct head posture during the recording of the image. In this way, inaccuracies resulting from such an incorrect head posture can thus still be corrected.

In some of the methods described above, as described the spectacle frame is identified in the recorded image and the thus determined location of the spectacle frame is used for determining the near-vision point. For this purpose, the person wears the spectacle frame during the recording of the image.

In other embodiments, a virtual model, in particular a 3D model, of the head of the person is used. A model of a spectacle frame can be adapted to the 3D model.

In some exemplary embodiments, the 3D model can be determined on the basis of recordings of the same camera unit such as is used for exemplary embodiments of various aspects of the disclosure as explained above and below. This can have the advantage that the 3D models thus determined can be compared with recordings of the camera unit more easily.

On the basis of these models (model of the head and the adapted model of the spectacle frame) and the viewing direction ascertained as described above, the near-vision point can then in turn be determined since the location of the spectacle lens planes and the eye centers of rotation can be inferred from the 3D model of the head with the adapted model of the spectacle frame. The eye centers of rotation can also be inferred from the 3D model of the head without the 3D model of the spectacle frame.

In some exemplary embodiments, the eye centers of rotation can be stored as metadata.

Metadata should be understood to mean data that contain items of information about the features of the model but not the model itself. In particular, the metadata can supply additional information concerning the models and/or contain prominent points or curves on the basis of the respective model, for example the eye center of rotation, which can be calculated on the basis of the model but is not part of the model. By way of example, in the model it is possible to identify the cornea and to determine the eye center of rotation on the basis of the spatial arrangement of the cornea. Metadata are also explained in general terms in the German "Metadaten" Wikipedia article, as of Jun. 7, 2018.

One advantage of the use of models is that it is possible to change rapidly between different spectacle frames, without an image recording having to be carried out again. It is assumed here that the viewing direction when looking at the near-vision target is independent of the spectacle frame worn.

A model, in particular a 3D model, should be understood to mean a representation, in the case of a 3D model a three-dimensional representation, of real objects which are present as a data set in a storage medium, for example a memory of a computer or a data carrier. By way of example, such a three-dimensional representation can a 3D mesh, consisting of a set of 3D points, which are also referred to as vertices, and connections between the points, which connections are also referred to as edges. In the simplest case, this connection form a triangle mesh. Such representation as a 3D mesh only describes the surface of an object and not the volume. The mesh need not necessarily be closed. Thus, if the head, for example, is described in the form of a mesh, it appears like a mask. Details in respect of such 3D models are found in Rau J-Y, Yeh P-C, "A Semi-Automatic Image-Based Close Range 3D Modeling Pipeline Using a Multi-Camera Configuration." Sensors (Basle, Switzerland). 2012; 12(8):11271-11293. doi:10.3390/s120811271; in particular page 11289, FIG. "FIG. 16".)

A voxel grid, which represents a volume-type representation, is a further option for representing a 3D model. Here, the space is divided into small cubes or cuboids, which are referred to as voxels. In the simplest case, the presence or absence of the object to be represented is stored in the form of a binary value (1 or 0) for each voxel. In the case of an edge length of the voxels of 1 mm and a volume of 300 mm×300 mm×300 mm, which represents a typical volume for a head, a total of 27 million such voxels is consequently obtained. Such voxel grids are described in, e.g., M. Nießner, M. Zollhöfer, S. Izadi, and M. Stamminger, "Real-time 3D reconstruction at scale using voxel hashing". ACM Trans. Graph. 32, 6, Article 169 (November 2013), available at the url doi.org/10.1145/2508363.2508374.

The spectacle lens plane denotes a plane which approximates the location of a respective spectacle lens (which is generally curved). It can be, in particular, a plane having a smallest deviation (for example according to the criterion of least squares) from the frame edge of the respective spectacle lens. The frame edge can be identified as described in EP 17153651.9. Alternatively, the plane of the lens shape in accordance with DIN EN ISO 13666:2012; 17.1 can be used as the spectacle lens plane. However, the determination of this plane of the lens shape presupposes, as in DIN EN ISO 13666:2012, knowledge of the shape of a dummy lens, while only the location of the frame edge is required in the case of the above definition.

The adaptation of the model of the spectacle frame to the model of the head can be carried out here as described in US 2003/0123026 A1, US 2002/105530 A1, US 2016/0327811 A1 or European patent application No. 17173929.5.

One embodiment involves determining the change in the head posture when looking at the near-vision target relative to the head posture when looking into the distance. This can be carried out by means of one or a plurality of images as described above, wherein in this case spectacles do not have to be worn by the person during the recording of the one or the plurality of images. The 3D model of the head can then be inclined in accordance with the change in the head posture or can be created on the basis of the images in the case of a plurality of cameras. By identifying mutually corresponding features in the recorded images, it is then possible to create the model taking account of the known recording positions (see e.g., H. Hirschmuller, "Stereo Processing by Semiglobal Matching and Mutual Information," in IEEE Transactions on Pattern Analysis and Machine Intelligence, vol. 30, no. 2, pp. 328-341, February 2008. doi: 10.1109/TPAMI.2007.1166). With the viewing direction—determined as described above—when looking at the near-vision target, following the virtual adaptation of the model of the spectacle frame it is then known where the distance and near-vision points lie, since e.g., the relative location of eye center of rotation and spectacle lens planes in accordance with the frame edges are thus known from the models.

Another embodiment involves determining the positions of the pupils in space for distance viewing direction and near viewing direction with the aid of image recordings. Together with the position of a further viewpoint, the model of the head can then be brought to a position corresponding to the head posture of the person when looking at the near-vision target. The tip of the nose or a point on the ears can be used as further viewpoint since the relative location of these points with respect to the pupils scarcely changes during movements. Otherwise the near-vision point is determined as described above.

Alternatively, the change in the head posture when looking at the near-vision target can also be effected only on the basis of lateral images of the head which are recorded when looking into the distance and when looking at the near-vision target. By identifying corresponding features in the lateral images (e.g., as described in the above reference Hirschmüller et al.), it is then possible to determine the change in the head inclination and apply it to the 3D model.

Lateral images of the head are images in which the head is visible from the side, substantially in the direction of a temple part of the head. In other words, the image recording in the case of lateral images is effected substantially in a direction corresponding to a connecting line between the ears of the head. Only one eye of the person is visible in a lateral image.

By contrast, front images are images in which the image recording is effected substantially perpendicularly to a plane defined by the eyes and the mouth. As a rule, both eyes, the nose and the mouth are imaged here.

Consequently, there are various possibilities for determining the location of the near-vision point on the basis of models of head and spectacle frame.

The use of a (real) spectacle frame in the image recordings can also be combined with the use of models of head and spectacle frame. In this case, the near-vision point is determined initially as described for the real spectacle frame. Results of this determination such as head posture and viewing direction can then be applied to the use of the models. Consequently, the results for the near-vision point can be applied to other spectacle frames by means of models thereof, without images having to be recorded again.

The position and/or orientation of the near-vision target can also be determined manually (for example using a meterstick) and then input manually. The position of the pupils can also be estimated.

In accordance with a further embodiment, provision is made of a computer program comprising a program code which, when executed on a computing unit, causes one of the methods described above to be provided.

In accordance with a further aspect, a device for determining a near-vision point is provided, comprising:
a movable near-vision target,
an image recording unit for recording an image of a head of a person while the person is looking at the near-vision target,
a position detection unit for determining a position and/or orientation of the near-vision target, and
a computing unit for determining the near-vision point on the basis of the image and the position and/or the orientation of the near-vision target.

Like the corresponding method described above, this device enables a free positioning of the near-vision target and thus adoption of a natural head posture during the determination of the near-vision point and also a determination of the near-vision point without measuring braces.

The device can be configured for carrying out one of the methods described above. In particular, for this purpose the image recording unit, as described above, can comprise two or more cameras, by means of which a front image and one or a plurality of lateral images are able to be recorded simultaneously. Moreover, the near-vision target can comprise the camera unit and/or location sensors as position detection unit, as described above. The position detection unit, as likewise described, can comprise mechanical sensors or one or a plurality of cameras. The computer program mentioned above can be stored in the device in order to be executed by the computing unit.

BRIEF DESCRIPTION OF THE DRAWINGS

The disclosure will now be described with reference to the drawings wherein.

DESCRIPTION OF EXEMPLARY EMBODIMENTS

Figure 1:
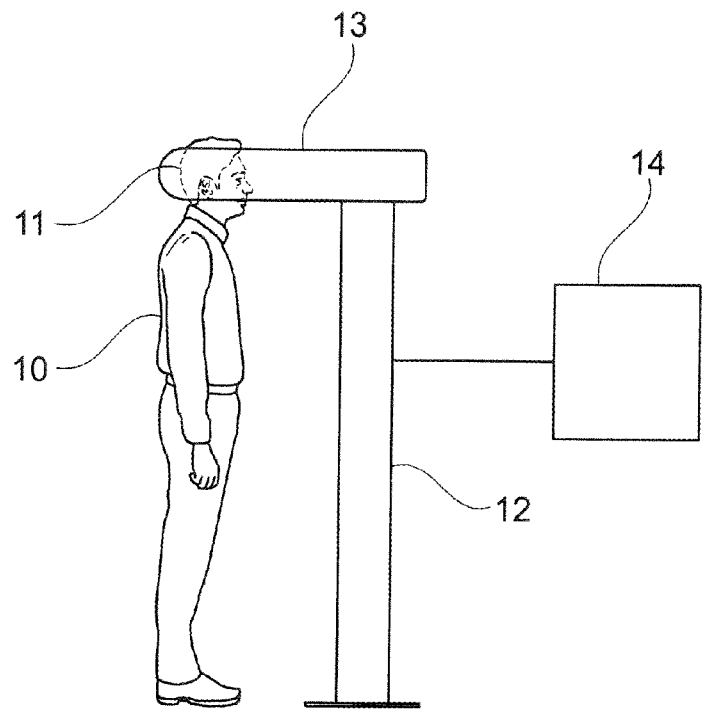
FIG. 1 shows a device in accordance with the related art for determining a distance-vision point, on the basis of which the disclosure can be implemented.
Figure 2:
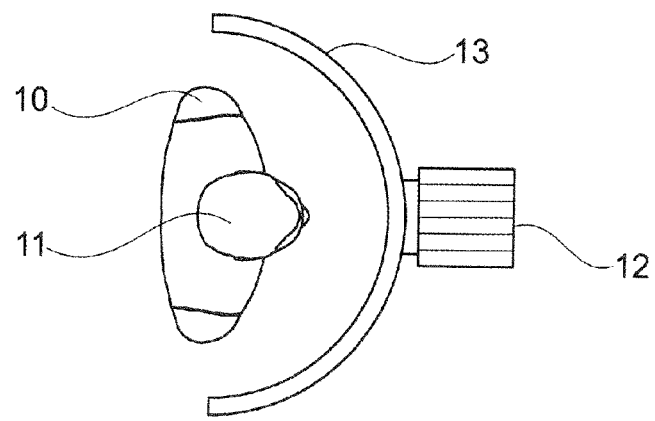
FIG. 2 shows a plan view of the device from FIG. 1.

FIG. 1 shows a side view of a device such as is described in greater detail in European patent applications 17 153 559.4 and 17 153 556.0, already cited. The present disclosure can be implemented as an extension on the basis of this device. FIG. 2 shows a plan view of the device from FIG. 1. The device comprises a camera unit 13 fitted on a column 12. The camera unit 13 comprises a plurality of cameras, inter alia a front camera for recording a front image of a head 11 of a person 10 to be examined and also lateral cameras for recording lateral images of the head 11. In FIGS. 1 and 2, the person 10 has a head posture for determining a distance-vision point, i.e. the person is looking substantially horizontally straight ahead at a target provided in the device. A computing unit 14 is connected to the device for evaluating the recorded images, in particular in order to determine the distance-vision points.

As explained in greater detail in this context in the European patent applications mentioned above, a location of a spectacle frame worn by the person 10 on the head 11 and also locations of the person's pupils are determined in the course of the determination of the distance-vision point. In this case, the location of the spectacle frame or at least of frame edges thereof and of the pupils and/or cornea can be effected manually by marking the spectacle frame and pupils in represented images or automatically by image processing algorithms, as likewise described. If the eye, for example the cornea of the eye, is not able to be identified accurately in the lateral images, since it is concealed by spectacle earpieces, an image of the head without spectacle frame can also additionally be inserted in order to enable the position of the pupil and/or the cornea to be determined. In this case, the determination of the position of the cornea and/or the pupil of the person can likewise be performed in an automated manner, as described previously for the case where the eyes are not concealed by the spectacle frame.

In this case, the image of the head without spectacle frame can be provided as a further lateral image on the basis of a 3D model of the head of the person. The 3D model of the head can be created on the basis of image recordings of the plurality of cameras of the camera unit 13, that is to say on the basis of a plurality of image recordings as explained in the introduction. The 3D model is created here without a spectacle frame, i.e. the image recordings for creating the 3D model record the person's head without the person wearing the spectacle frame.

To that end, the further lateral image is generated on the basis of the 3D model of the head using techniques of image synthesis (rendering) as though the observer viewed the head from which the 3D model was generated from the location at which the camera (e.g., of the camera unit 13) that records the lateral image is situated. In other words, the recording direction when recording the lateral image corresponds to the viewing direction with regard to the further lateral image. Image synthesis is understood here generally to mean the generation of graphics from a model, see e.g., the German Wikipedia article "Bildsynthese".

The lateral image and the further lateral image are then brought to congruence, i.e. adapted to one another in terms of size, position and orientation. For this purpose, specific points or image regions can be identified by conventional image processing methods in the lateral image and the further lateral image and can then be brought to congruence, i.e. the points or regions are brought to the same position. Suitable points include the tip of the nose or the tip of the chin. Suitable image regions include the forehead or the chin. One possible variant in this respect is described in more specific detail below:

Proceeding from an initial position of the 3D model of the head, the 3D model of the head can be brought to an end position of the head by means of a transformation with a translation and a rotation. Such a transformation of the head is also referred to as orientation.

In this case, the initial position can be predefined by the coordinate origin of the 3D model and the choice of coordinate directions, e.g., head-fixed axes vertical/horizontal lateral/horizontal frontal.

Transformation is understood to mean measure-preserved coordinate transformations, for example a rotation by up to three spatial angles and a translation along up to three coordinate axes.

Parameters T of the translation, that is to say magnitude and direction of the translation (for example expressed by displacements along three coordinate axes), and parameters R of the rotation, that is to say the magnitude of the rotation (for example expressed by rotation angles about the three coordinate axes), can be determined in an automated manner or manually.

For this purpose, both in the case of automated determination and in the case of manual determination, it is possible to identify characteristic regions, for example characteristic points, contours or areas in the lateral image or else other image recordings for the further lateral image on the basis of the 3D model or other images of the person generated on the basis of the 3D model, which are identifiable both with and without spectacles and are ideally uninfluenced by facial expressions. They can be for example: base of the ears, nose, contour of forehead/nose/chin viewed from the side. However, other characteristic regions are also possible. During automatic orientation, the features which are selected can be left to an algorithm. The orientation can be carried out iteratively. The translation can be carried out by means of a centroid determination in a first step, for example by determining a centroid of at least one portion of the coordinates of the 3D model and creating a second 3D model of a person wearing a spectacle frame, as described above, and likewise determining a centroid for the second 3D model. The parameters T of the translation can then be determined as the vectoral difference between the centroids from the first and second 3D models, or the parameters T can be used as an initial value for a more accurate determination of the parameters T, for example manually or by means of further algorithms.

The parameters R of the rotation can correspondingly be determined by means of a second orientation on the basis of the lateral image and the further lateral image. In this case, once again the location of the characteristic regions can be determined and a rotation of the head and the lateral inclination thereof can be deduced as a result.

In some exemplary embodiments, particularly if the 3D model was created using the same camera unit 13 as for the lateral image, the further lateral image is of the same size as the lateral image. If appropriate, the distance and/or the image angle of the virtual camera from which the further lateral image is generated by image synthesis can be adapted correspondingly to the 3D model. Consequently, no scaling is required here.

In other exemplary embodiments, it is possible to adapt the size of the representation of an image generated from the 3D model like the further lateral image, for example by means of a scaling of the 3D model or of images generated therefrom like the further lateral image.

The ascertained transformation can also be applied to metadata of the 3D model, for example the eye centers of rotation. For an eye center of rotation Pi in the 3D model, the following then holds true for the transformed position Pi':

$$Pi'=(T+R)Pi.$$

On the basis of the transformed positions Pi' of the eye centers of rotation, the near-vision points can then be determined as points of intersection between viewing direction vectors attached to the eye centers of rotation (i.e. the viewing direction seen as vector) and the spectacle lens planes.

This bringing to congruence is possible in particular even if both of the person's eyes are concealed in the lateral image, for example by nose and spectacle earpieces as mentioned above, by virtue of the use of points or image regions, as discussed above, which are present both in the lateral image and in the further lateral image. The position of the cornea and/or of the pupil of the person can thus be determined on the basis of the further lateral image since this position is known in the 3D model and thus also in the further lateral image. This determination can be carried out in an automated manner.

The ascertained position of cornea and/or pupil can then additionally be represented in the lateral image, with the result that the ascertained position can be confirmed and/or corrected by the optician. It is likewise possible for the optician to reject the ascertained position and to repeat the measurement. For this purpose, optionally, the entire further lateral image can be displayed as superimposed on the lateral image, or only a region of the further lateral image, for example the region representing the cornea and/or the pupil, can be laid over the lateral image. In particular, for this representation, at least one part of the lateral image can be replaced by a corresponding part of the further lateral image that comprises the pupil and/or cornea. In this case, a corresponding part is a part that shows the same part of the head.

In particular, for the representation and/or further processing, for example by means of the previously described automated methods for determining the pupil and/or cornea positions, at least one portion of the pixels of the lateral image can be replaced by pixels of the further lateral image.

Moreover, as already explained above, a location of an eye center of rotation is estimated. After these measurements, therefore, a relative location of the eye center of rotation with respect to the spectacle frame and also a shape of the spectacle frame are known. In this case, the location of the spectacle frame determines the location of the spectacle lenses and thus of planes in which the spectacle lenses lie (also referred to as lens planes). With these data, distance-vision points can then be determined in the manner described in the European patent applications mentioned above.

Figure 3A:
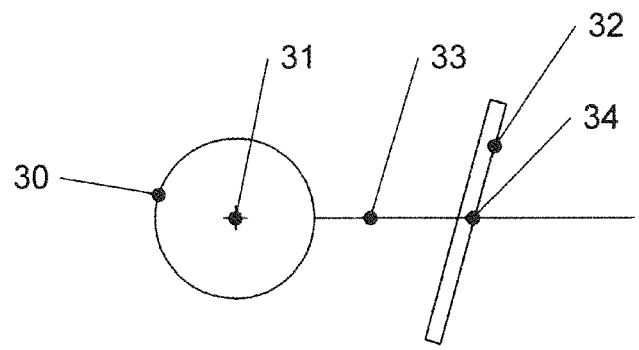
FIGS. 3A and 3B show explanatory views for determining a distance-vision point.
Figure 3B:
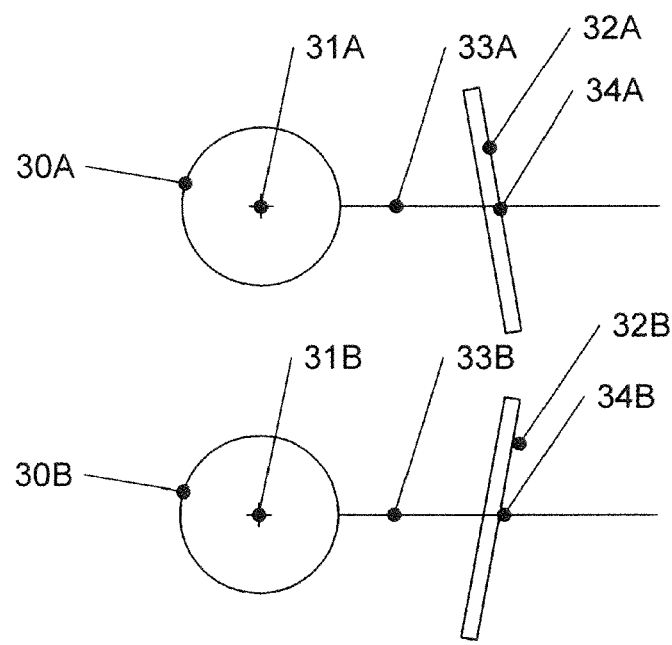

This information is then used in the described exemplary embodiment for determining one or both near-vision points. Moreover, distance-vision points can be determined as described in the European patent applications. This is illustrated schematically in FIGS. 3A and 3B. FIG. 3A shows a location of a distance-vision point 34 for a viewing direction 33 proceeding from an eye center of rotation 31 of an eye 30 as point of intersection of the viewing direction 33 with a spectacle lens 32, in side view. FIG. 3B shows a plan view for both eyes, the reference signs for the left eye each having an appended A, and the reference signs for the right eye an appended B, and otherwise corresponding to the reference signs in the side view in FIG. 3A.

In this case, the location of the spectacle lenses 32 results from the spectacle frames identified in the image recordings, in particular from the frame edges thereof.

Figure 4:
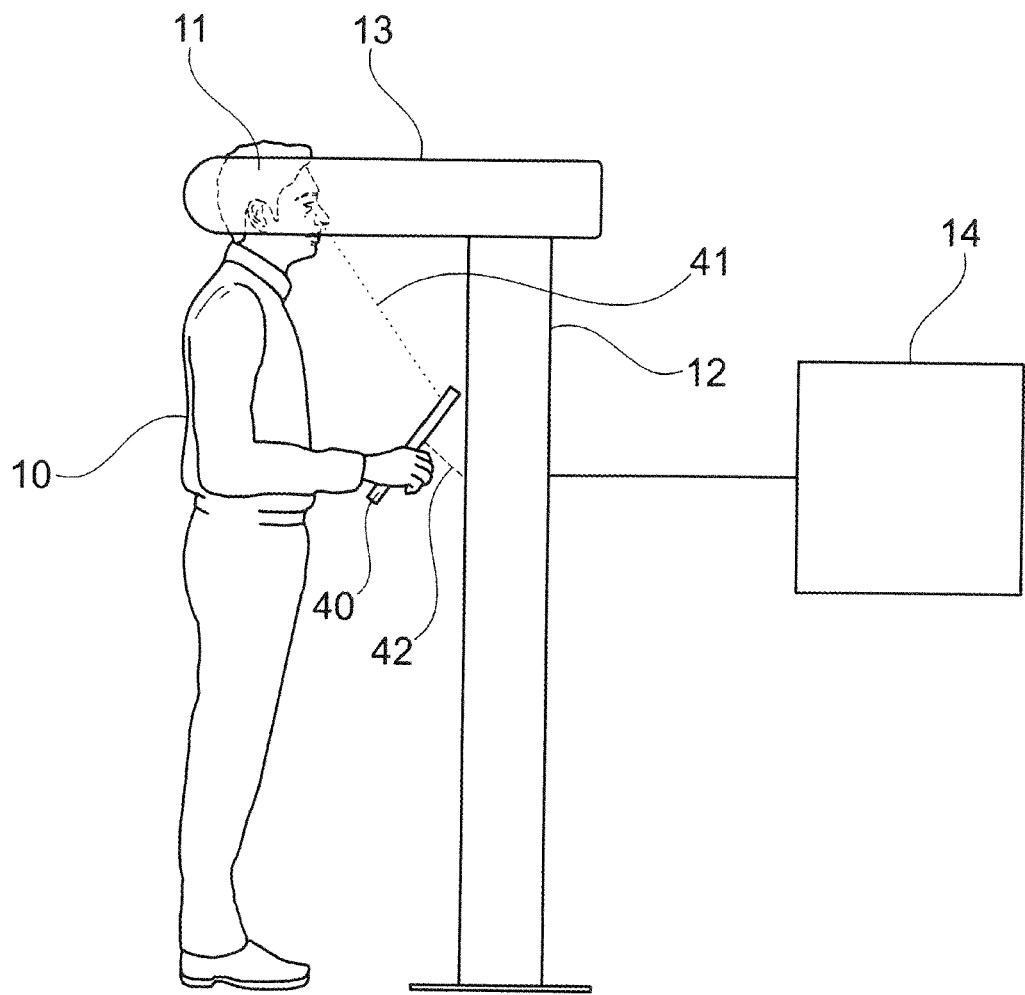
FIG. 4 shows an extension of the device from FIG. 1 for a determination of a near-vision point in accordance with one exemplary embodiment of the present disclosure.

FIG. 4 shows a side view of the device from FIG. 1 augmented for a determination of a near-vision point according to the disclosure. Here, in addition to the device from FIG. 1, a near-vision target 40 is provided for the person 10, the near-vision target having a text to be read and also being referred to as reading target. In this case, the near-vision target 40 is movable by the person 10 in order to bring it to a position corresponding to a pleasant reading posture. The reference sign 41 denotes the viewing direction of the person 10 when reading the text. In the exemplary embodiment in FIG. 4, the near-vision target 40 is connected to the column 12 by a movable connection 42 comprising one or more sensors. The position of the near-vision target 40 is detected by means of these sensors. In this case, the at least one sensor can be configured to provide a signal to a computing unit 14 on the basis of the position of the movable connection 42. In addition, image recordings of the head 11 are performed by the camera unit 13 in the position illustrated in FIG. 4. The spectacle frame is in turn identified in the image recordings. This can be done jointly with the identification of the spectacle frame for the recordings from FIG. 1 or after this, the spectacle frame determined in FIG. 1 being used as a basis in the latter case. By way of example, models for spectacle frames as described in European patent application 17 153 538.8 can be used here as boundary conditions.

Figure 5A:
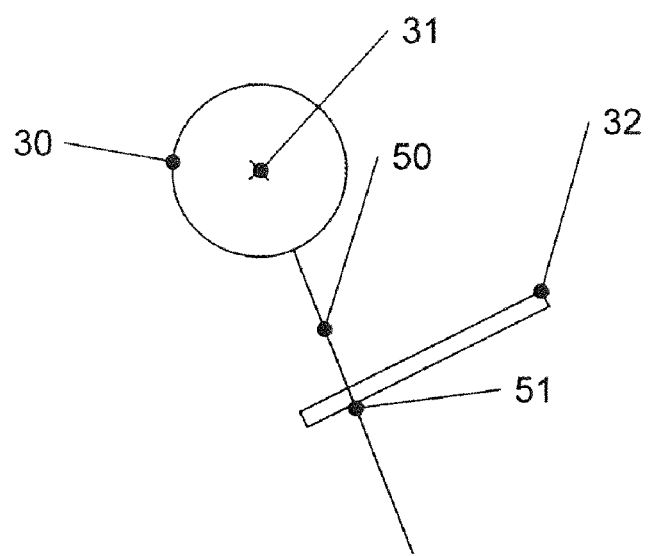
FIGS. 5A and 5B show diagrams for elucidating the determination of near-vision points in accordance with exemplary embodiments of the disclosure.
Figure 5B:
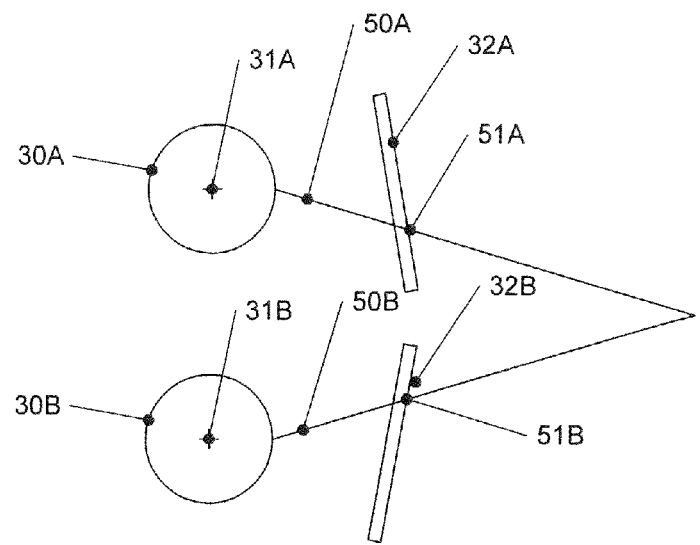

As a supplementation to the conventional device from FIG. 1, the computing unit 14 is then also programmed to determine near-vision points for both eyes. In this case, the relative location of the eye center of rotation with respect to the frame ascertained during the determination of the distance-vision points in the position in FIG. 1 is applied to the location of the spectacle frame then determined and the difference between the position of the eye center of rotation and the position of the near-vision target 40 is used as viewing direction. The viewing direction 41 is thus determined. The viewing direction 41 proceeding from the eye center of rotation then intersects the spectacle lenses, the locations of which are defined by the location of the spectacle frame, at the near-vision points. This is illustrated schematically in FIGS. 5A and 5B. In this case, FIGS. 5A and 5B show views corresponding to FIGS. 3A and 3B for the determination of near-vision points 51 in FIG. 5A and 51A, 51B in FIG. 5B. The viewing direction 50 (50A, 50B for left and right eyes) intersect(s) the spectacle lenses 32A, 32B at the near-vision points 51A, 51B, which differ from the distance-vision points, as evident from a comparison of FIGS. 5A, 5B with FIGS. 3A, 3B.

As already explained in the introduction, as an alternative to the determination of the position of the near-vision target 40 and the image recording by the camera unit 13, an image recording by means of the near-vision target and a determination of the orientation of the near-vision target can be effected. A corresponding near-vision target is illustrated in FIG. 6.

Figure 6:
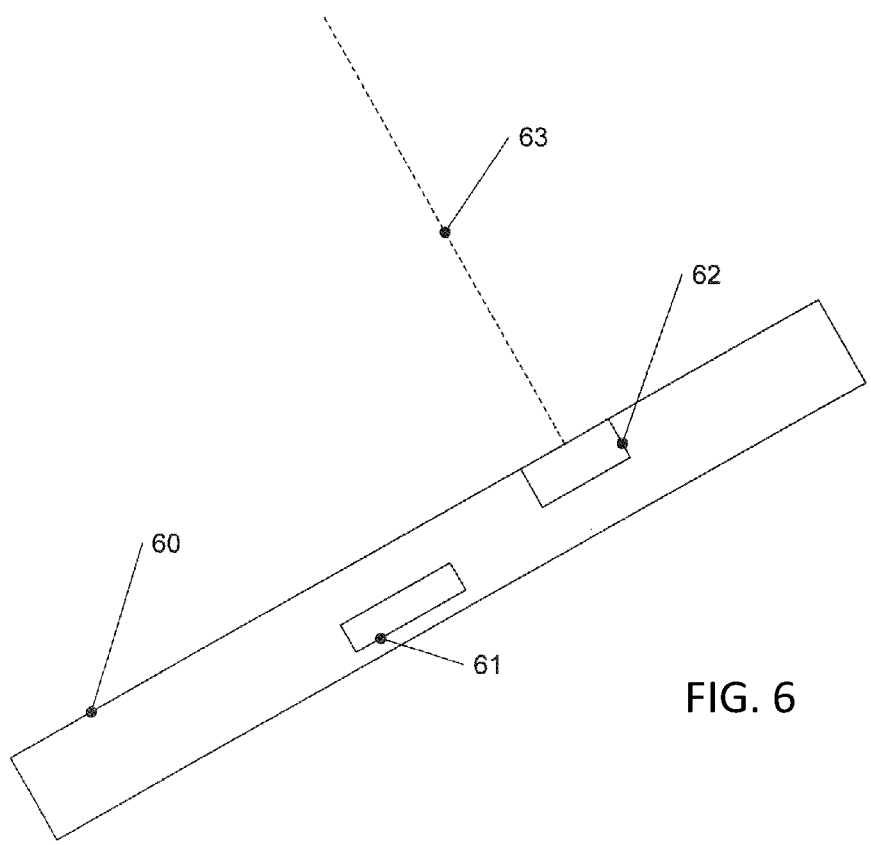
FIG. 6 shows a schematic view of a near-vision target in accordance with one exemplary embodiment.

FIG. 6 shows a near-vision target 60 having a built-in camera 62. The camera 62 has an axis of symmetry 63 corresponding to the optical axis of the camera 62. Furthermore, the near-vision target 60 has an inclination sensor 61.

In this case, the near-vision target 60 is a tablet computer or smartphone, which usually have inclination sensors and built-in cameras. In the case of the embodiment in FIG. 6, an image of the head of the person is recorded by means of the camera 62 while the person views the near-vision target 60. From the orientation of the near-vision target 60 as determined by the inclination sensor 61 and thus from the orientation of the axis of symmetry 63, the properties of the camera 62 (image angle and resolution) and the recorded image, it is then possible, as described, to determine the viewing direction of the person, and then, as described above, the near-vision points on the basis of the viewing direction.

Figure 7:
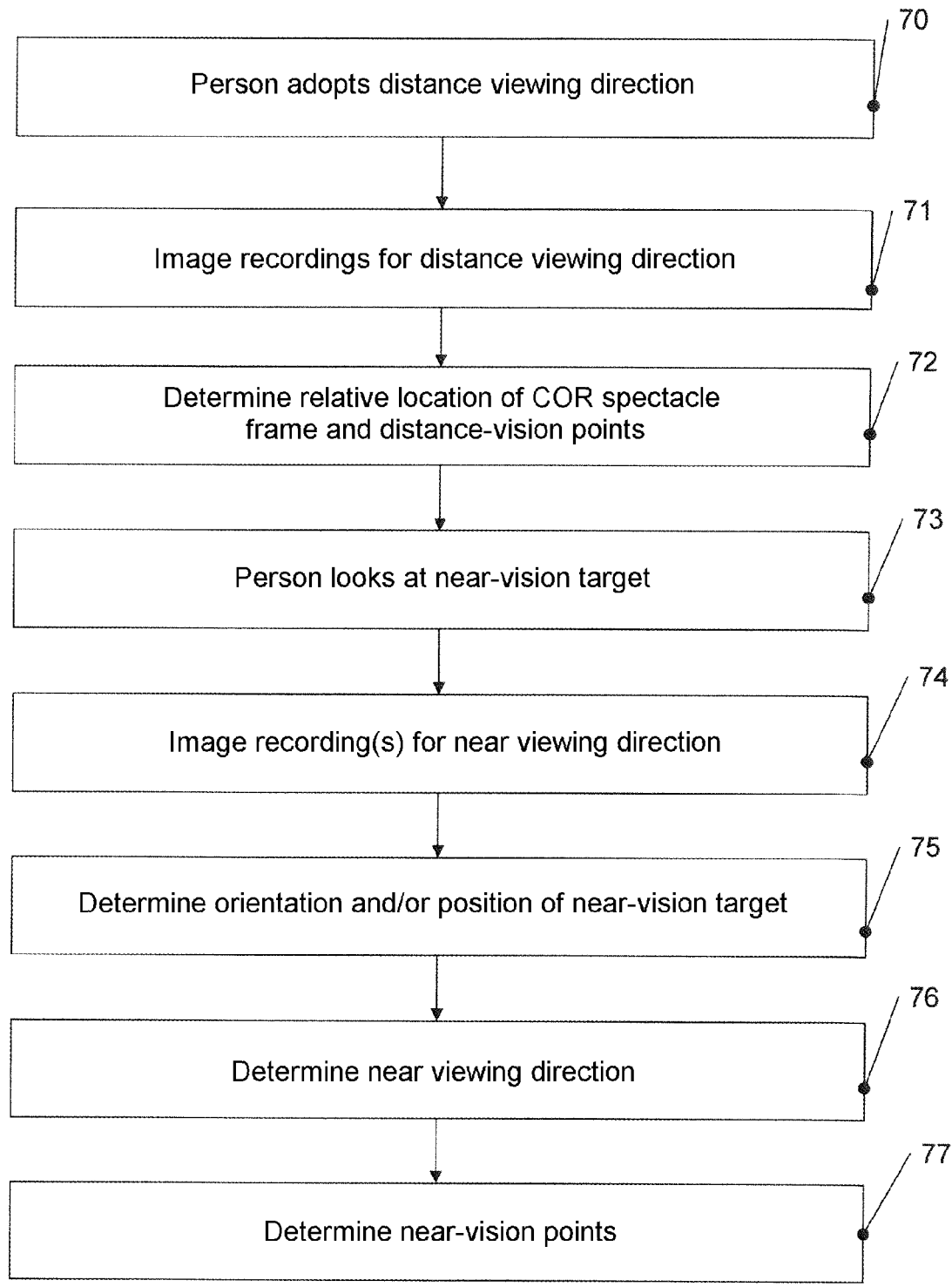
FIG. 7 shows a flow diagram of a method in accordance with one exemplary embodiment.

FIG. 7 shows a flow diagram of a method in accordance with one exemplary embodiment. The method in FIG. 7 will be explained with reference to the devices illustrated in FIGS. 1 to 6, for the purpose of better elucidation.

In step 70, a person to be examined adopts a distance viewing direction, for example the position illustrated in FIGS. 1 and 2, in which the user looks straight horizontally forward. In step 71, image recordings for the distance viewing direction are then effected, by means of the camera unit 13 in the case of FIGS. 1 and 2. From these image recordings, in step 72, the location of a spectacle frame, the location of pupils and therefrom the relative location of the eye center of rotation (COR) with respect to the spectacle frame are determined as already described. In addition, in step 72, distance-vision points are determined as explained in FIGS. 3A and 3B.

In step 73, the person then looks at a near-vision target, as is shown for the near-vision target 40 in FIG. 4, or at the near-vision target 60 from FIG. 6. In step 74, one or a plurality of image recordings for the near viewing direction are then effected, for example a plurality of image recordings by means of the camera unit 13 from FIG. 4 or one image recording by means of the camera 62 of the near-vision target 60 from FIG. 6. Step 75 involves determining orientation (for example by means of the location sensor 61) and/or position (for example by means of the sensors of the connection 42 from FIG. 4) of the near-vision target. From the data thus ascertained, in step 76, the near viewing direction is determined as described. Optionally, in step 76, the near viewing direction can additionally be corrected by a user such as an optician. This correction can be effected in different directions, for example if the person did not adopt a natural head posture at the time of the image recording. In step 77, near-vision points are then determined by the intersection of the near viewing direction proceeding from the eye center of rotation with the spectacle lenses, as is shown in FIGS. 5A and 5B.

In this case, the camera unit 13 has intrinsically and extrinsically calibrated cameras, i.e. the location of the cameras with respect to one another and also their directions and properties are known, and for example image field distortions can be extracted computationally.

At least some possible exemplary embodiments are specified below:

Clause 1. A method for determining a near-vision point (51), comprising:
  recording an image of a head of a person while the person is looking at a near-vision target (40; 60),
  characterized
  in that the near-vision target (40; 60) is movable, and in that the method further comprises:
    determining a position and/or orientation of the near-vision target (40; 60), and determining the near-vision point (51) on the basis of the image and on the basis of the position and/or orientation of the near-vision target (40; 60).

Clause 2. The method according to clause 1, further comprising:
determining a viewing direction of the person when looking at the near-vision target on the basis of the image, wherein determining the near-vision point is carried out on the basis of the viewing direction.

Clause 3. The method according to clause 2, further comprising determining a relative location of a spectacle frame with respect to an eye center of rotation of the person,
wherein the near-vision point is determined by ascertaining a point of intersection of a line in the viewing direction proceeding from the eye center of rotation with a location of a spectacle lens plane (32), the location being defined by the location of the spectacle frame.

Clause 4. The method according to clause 3, wherein determining the relative location of the spectacle frame with respect to the eye center of rotation is carried out on the basis of further image recordings.

Clause 5. The method according to clause 4, further comprising determining a distance-vision point on the basis of the further image recordings.

Clause 6. The method according to clause 4 or 5, further comprising determining the location of the spectacle frame on the basis of the further image recordings.

Clause 7. The method according to clause 6, further comprising determining a location of the spectacle frame in the recorded image, wherein determining the near-vision point is carried out on the basis of the location of the spectacle frame in the recorded image.

Clause 8. The method according to clause 7, wherein determining the location of the spectacle frame in the recorded image is carried out on the basis of determining the location of the spectacle frame in the further image recordings or at the same time as determining the location of the spectacle frame in the further image recordings.

Clause 9. The method according to any of clauses 5-8, wherein recording the image is carried out by an image recording unit (13; 62), wherein the further image recordings are carried out by the same image recording unit (13; 62) used for recording the image.

Clause 10. The method according to any of clauses 2-8, wherein recording the image is carried out by a camera incorporated in the near-vision target, wherein determining the viewing direction is carried out when looking at the near-vision target on the basis of the orientation of the near-vision target and the recorded image.

Clause 11. The method according to any of clauses 2-10, wherein the method comprises correcting the determined viewing direction and/or correcting the determined near-vision point.

Clause 12. The method according to any of clauses 2-11, wherein determining the near-vision point is carried out on the basis of the determined viewing direction and a model of the head to which a model of a spectacle frame is adapted.

Clause 13. A computer program comprising a program code which, when executed on a processor, causes the method according to any of clauses 1-12 to be carried out.

Clause 14. A device for determining a near-vision point, comprising:
a near-vision target (40; 60), and
an image recording unit (13; 62) for recording an image of a person while the person is looking at the near-vision target,
characterized in that the near-vision target (40; 60) is movable, and in that the device further comprises:
a position detection unit (42; 61) for determining a position and/or orientation of the near-vision target, and
a computing unit (14) for determining the near-vision point on the basis of the image and the position and/or orientation of the near-vision target (40; 60).

Clause 15. The device according to clause 14, characterized in that the near-vision target (60) comprises the image recording unit (62) and the position detection unit (61).

The foregoing description of the exemplary embodiments of the disclosure illustrates and describes the present disclosure. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A method for determining a near-vision point, the method comprising:
recording an image of a head of a person with a camera incorporated in a near-vision target while the person is looking at the near-vision target,
wherein the person is optionally wearing a spectacle frame,
wherein the image shows at least one of a pupil position or a cornea position of an eye, and
wherein the near-vision target is movable;
determining an orientation of the near-vision target;
determining a viewing direction of the person when looking at the near-vision target on a basis of the image;
determining the near-vision point on the basis of the image, on the basis of the viewing direction, and a location of a spectacle frame, wherein, if the person is wearing the spectacle frame, the location of the spectacle frame is determined from the image, and, if the person is not wearing the spectacle frame, the location of the spectacle frame is determined virtually on a basis of a model; and
identifying a location of at least one of a pupil position or a cornea position of the eye relative to an axis of symmetry of the camera and an image angle and a resolution of the camera, wherein the direction of the axis of symmetry is determined by the orientation of the near-vision target.

2. A method for determining a near-vision point, the method comprising:
recording an image of a head of a person with a camera incorporated in a near-vision target while the person is looking at the near-vision target,
wherein the person is optionally wearing a spectacle frame, wherein the image shows at least one of a pupil position or a cornea position of an eye, and
wherein the near-vision target is movable;
determining an orientation of the near-vision target;
determining a viewing direction of the person when looking at the near-vision target on a basis of the image;
determining the near-vision point on the basis of the image, on the basis of the viewing direction, and a location of a spectacle frame, wherein, if the person is wearing the spectacle frame, the location of the spectacle frame is determined from the image, and, if the person is not wearing the spectacle frame, the location of the spectacle frame is determined virtually on a basis of a model; and
identifying a location of at least one of a pupil position or a cornea position in the image and determining the viewing direction relative to an axis of symmetry of the camera with a fixed relationship between an angle between an object in the image and the axis of symmetry of the camera as viewed from the camera and a pixel or pixels at which the object appears in the image, wherein the fixed relationship is given by a resolution and an image angle of the camera.

3. The method as claimed in claim 1, wherein the near-vision target comprises a display region, wherein the recording is carried out while the person is looking at the display region of the near-vision target, and wherein determining the viewing direction is additionally based on a distance between the camera and the display region.

4. The method as claimed in claim 1, further comprising:
recording a first lateral image of the head of the person; and
generating a second lateral image of the head of the person on a basis of a 3D model of the head,
wherein the location of the at least one of the pupil position or the cornea position relative to the axis of symmetry of the camera additionally is determined on the basis of the first lateral image and the second lateral image.

5. The method as claimed in claim 1, the method further comprising:
determining an eye center of rotation on the basis of the at least one of the pupil position or the cornea position, wherein determining the viewing direction is additionally based on the eye center of rotation.

6. The method as claimed in claim 2, wherein the near-vision target comprises a display region,
wherein the recording is carried out while the person is looking at the display region of the near-vision target, and
wherein determining the viewing direction is additionally based on a distance between the camera and the display region.

7. A method for determining a near-vision point, the method comprising:
recording a front image and a first lateral image of a head of a person while the person is wearing a spectacle frame and looking at a near-vision target, wherein the near-vision target is movable;
determining a position and an orientation of the near-vision target;
determining a location of the spectacle frame on a basis of the front image and the lateral image;
determining a viewing direction of the person when looking at the near-vision target, and determining the near-vision point of the spectacle frame on the basis of the viewing direction and the location of the spectacle frame;
generating a second lateral image of the head on the basis of a 3D model of the head;
determining a position of at least one of a pupil or a cornea of an eye of the person on the basis of the first lateral image and the second lateral image; and
calculating the viewing direction as a difference between the position of the near-vision target and the position of the pupil or the cornea.

8. The method as claimed in claim 7, wherein the second lateral image is generated as though an observer viewed the head from which the 3D model was generated from the location from which the camera recorded the first lateral image.

9. The method as claimed in claim 7, further comprising:
determining the position of the at least one of the pupil or the cornea on the basis of the first lateral image and the second lateral image by bringing the first lateral image to congruence with the second lateral image.

10. The method as claimed in claim 7, further comprising:
determining the position of the at least one of the pupil or the cornea on the basis of the first lateral image and the second lateral image by replacing a part of the first lateral image with a corresponding part of the second lateral image that includes the at least one of the pupil or the cornea.

11. A method for determining a near-vision point with a camera device and a near-vision target, the method comprising:
recording an image of a head of a person while the person is looking at the near-vision target with the camera device,
wherein the person is optionally wearing a spectacle frame,
wherein the near-vision target is movably attached to a column with a movable mechanical connection, and
wherein the near-vision target has at least one sensor;
determining at least one of a position or an orientation of the near-vision target in space with the at least one sensor; and
determining the near-vision point on the basis of the image, on the basis of the at least one of the position or the orientation of the near-vision target, and on the basis of a location of the spectacle frame, wherein, if the person is wearing the spectacle frame, the location of the spectacle frame is determined from the image, and, if the person is not wearing the spectacle frame, the location of the spectacle frame is determined virtually on the basis of a model.

12. The method as claimed in claim 11, wherein the sensor is configured to provide a signal on the basis of the position of the movable mechanical connection.

13. The method as claimed in claim 11, further comprising:
determining a viewing direction of the person when looking at the near-vision target on the basis of the image, wherein determining the near-vision point is additionally based on the viewing direction.

14. The method as claimed in claim 13, wherein recording the image is carried out by a camera incorporated in the near-vision target, and
wherein determining the viewing direction is carried out when looking at the near-vision target on the basis of the orientation of the near-vision target and the recorded image.

15. The method as claimed in claim 10, further comprising:
determining a relative location of a spectacle frame with respect to an eye center of rotation of the person,
wherein the near-vision point is determined by ascertaining a point of intersection of a line in the viewing direction proceeding from the eye center of rotation with a location of a spectacle lens plane, the location being defined by the location of the spectacle frame.

16. The method as claimed in claim 15, wherein determining the relative location of the spectacle frame with respect to the eye center of rotation is carried out on the basis of further image recordings.

17. The method as claimed in claim 16, further comprising:
determining a distance-vision point on the basis of the further image recordings.

18. The method as claimed in claim 16, further comprising:
determining a location of the spectacle frame in a recorded image,
wherein determining the near-vision point is additionally carried out on the basis of the location of the spectacle frame in a recorded image.

19. The method as claimed in claim 18, wherein determining the location of the spectacle frame in a recorded image is carried out on the basis of determining the location of the spectacle frame in the further image recordings.

20. The method as claimed in claim 16, wherein the image is recorded with an image recording unit, and wherein the further image recordings are carried out by a same image recording unit used for recording the image.

21. The method as claimed in claim 11, further comprising:
correcting at least one of the determined viewing direction or a determined near-vision point.

22. The method as claimed in claim 13, wherein determining the near-vision point is additionally carried out on the basis of a determined viewing direction and a model of the head to which a model of a spectacle frame is adapted.

23. A computer program stored on a non-transitory storage medium and comprising a program code which, when executed on a processor, causes the method as claimed in claim 1 to be carried out.

24. A device for determining a near-vision point, the device comprising:
a near-vision target having an image recording unit and a position detection unit;
wherein the near-vision target is movable,
wherein the image recording unit is configured to record an image of a person while the person is looking at the near-vision target,
wherein the person is optionally wearing a spectacle frame, and
wherein the position detection unit is configured to determine an orientation of the near-vision target; and
a computing unit configured to determine a viewing direction of the person when looking at the near-vision target on the basis of the image,
wherein the computing unit is further configured to determine the near-vision point on a basis of the image, on the basis of the viewing direction and on the basis of a location of a spectacle frame, wherein, if the person is wearing the spectacle frame, the location of the spectacle frame is determined from the image, and, if the person is not wearing a spectacle frame, the location of the spectacle frame is determined virtually on the basis of a model, wherein determining the viewing direction is based on a location of the pupil position of the eyes relative to an axis of symmetry of the camera and an image angle and a resolution of the camera, and wherein the direction of the axis of symmetry is determined by the orientation of the near-vision target.

25. A device for determining a near-vision point, the device comprising:
a near-vision target having an image recording unit and a position detection unit,
wherein the near-vision target is movable, wherein the image recording unit is configured to record an image of a person while the person is looking at a near-vision target and is optionally wearing a spectacle frame, and
wherein the position detection unit is configured to determining an orientation of the near-vision target;
a computing unit configured to determine a viewing direction of the person when looking at the near-vision target on the basis of the image,
wherein the computing unit is further configured to determine the near-vision point on the basis of the image, on the basis of the viewing direction, and on the basis of a location of a spectacle frame, wherein, if the person is wearing the spectacle frame, the location of the spectacle frame is determined from the image, and, if the person is not wearing a spectacle frame, the location of the spectacle frame is determined virtually on the basis of a model, wherein determining the viewing direction includes identifying a location of at least one of a pupil position or a cornea position in the image and determining the viewing direction relative to an axis of symmetry of the camera with a fixed relationship between an angle between an object in the image and the axis of symmetry of the camera as viewed from the camera and the pixel or pixels at which the object appears, which relationship is given by resolution and image angle of the camera.

26. The device as claimed in claim 24, wherein the device is further configured to:
record a first lateral image of the head of the person; and
generate a second lateral image of the head of the person on the basis of a 3D model of the head,
wherein the location of the at least one of the pupil position or the cornea position relative to the axis of symmetry of the camera additionally is determined on the basis of the first lateral image and the second lateral image.

27. A device for determining a near-vision point, the device comprising:
a near-vision target, wherein the near-vision target is movable;
an image recording unit configured to record a front image and a first lateral image of a head of a person while the person is looking at the near-vision target and is wearing a spectacle frame;
a position detection unit configured to determine a position and an orientation of the near-vision target; and
a computing unit configured to:
determine a location of the spectacle frame on the basis of the front image and the lateral image,
determine a viewing direction of the person when looking at the near-vision target, and determine the near-vision point of the spectacle frame on the basis of the viewing direction and the location of the spectacle frame, wherein the computing unit is further configured to:

generate a second lateral image of the head on the basis of a 3D model of the head;

determine the position of at least one of a pupil or a cornea of an eye of the person on the basis of the first lateral image and the second lateral image, and calculate the viewing direction as a difference between the position of the near-vision target and the position of the pupil or the cornea and.

28. The device as claimed in claim 27, wherein the second lateral image is generated as though an observer viewed the head from which the 3D model was generated from the location from which a camera recorded the first lateral image.

29. The device as claimed in claim 24, wherein the device is configured to carry out a method comprising:

recording the image of the head of the person with the camera incorporated in the near-vision target while the person is looking at the near-vision target, wherein the image shows the at least one of the pupil position or the cornea position of the eye;

determining the orientation of the near-vision target;

determining the viewing direction of the person when looking at the near-vision target on the basis of the image;

determining the near-vision point on the basis of the image, on the basis of the viewing direction, and the location of a spectacle frame, wherein, if the person is wearing the spectacle frame, the location of the spectacle frame is determined from the image, and, if the person is not wearing the spectacle frame, the location of the spectacle frame is determined virtually on a basis of a model; and identifying the location of the at least one of a pupil position or a cornea position of the eye relative to the axis of symmetry of the camera and the image angle and the resolution of the camera, wherein the direction of the axis of symmetry is determined by the orientation of the near-vision target.

* * * * *

UNITED STATES PATENT AND TRADEMARK OFFICE
CERTIFICATE OF CORRECTION

PATENT NO. : 10,890,784 B2
APPLICATION NO. : 16/707112
DATED : January 12, 2021
INVENTOR(S) : Michael Gamperling, Cristina Alvarez Diez and Carsten Glasenapp It is certified that error appears in the above-identified patent and that said Letters Patent is hereby corrected as shown below:

In the Specification

Column 3, Line 14, change "device method" to -- device --.

Column 3, Line 23, change "device method" to -- device --.

Column 9, Line 23, change "PTZ Funktionalitat" to -- PTZ Funktionalität --.

Column 12, Line 29, change "Hirschmuller" to -- Hirschmüller --.

In the Claims

Column 24, Line 20, Claim 25, change "determining" to -- determine --.

Column 25, Line 12, Claim 27, change "cornea and." to -- cornea. --.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*